United States Patent [19]
Ackermann

[11] Patent Number: 5,510,609
[45] Date of Patent: Apr. 23, 1996

[54] ELECTRICALLY CONTROLLABLE OPTICAL FILTER ELEMENT

[75] Inventor: Emil Ackermann, Wattwil, Switzerland

[73] Assignee: Optrel AG, Wattwil, Switzerland

[21] Appl. No.: 301,357

[22] Filed: Sep. 6, 1994

[30] Foreign Application Priority Data

Sep. 13, 1993 [DE] Germany ............... 43 30 817.1

[51] Int. Cl.[6] ........................................ G01J 1/20
[52] U.S. Cl. .................... 250/201.1; 250/203.4; 359/275; 359/604
[58] Field of Search ................. 250/201.1, 205, 250/204, 203.2, 203.4, 206, 214 AL; 359/602, 603, 604, 608, 230, 267, 275, 229; 345/87

[56] References Cited

U.S. PATENT DOCUMENTS

| | | | |
|---|---|---|---|
| 4,724,311 | 2/1988 | Mechlenburg | 250/201.1 |
| 4,920,257 | 4/1990 | Fuerthbauer et al. | 250/201.1 |
| 5,258,607 | 11/1993 | Agostini et al. | 250/201.1 |
| 5,397,888 | 3/1995 | Muramatsu | 250/205 |

Primary Examiner—Edward P. Westin
Assistant Examiner—Que T. Le
Attorney, Agent, or Firm—Tarolli, Sundheim & Covell

[57] ABSTRACT

The anti-dazzle assembly comprises an optical filter element whose optical transmission is electrically controllable and an electronic control unit including a light sensitive sensor operatively connected to the optical filter element. The electronic control unit is adapted to vary the optical transmission of the optical filter element in response to the amount of light falling on the light sensitive sensor. This anti-dazzle assembly is controlled such that the intensity of light falling on the exposed surface of the sensor is selectively measured at a plurality of different area portions of this surface. The highest value is selected and used to influence the degree of optical transmission of the filter element. In this way, the anti-dazzle assembly can be controlled much more efficiently insofar as the dangerous high intensity point-shaped light sources are clearly recognized, but strong ambient light does not have a negative influence on the control of the filter element.

9 Claims, 2 Drawing Sheets

ELECTRICALLY CONTROLLABLE OPTICAL FILTER ELEMENT

FIELD OF THE INVENTION

The present invention refers to a method for controlling an anti-dazzle assembly, comprising an optical filter element whose optical transmission is electrically controllable, and an electronic control unit including a light sensitive sensor operatively connected to the optical filter element, whereby the electronic control unit is adapted to vary the optical transmission of the filter element in response to the amount of light falling on the light sensitive sensor. Furthermore, the invention refers to an anti-dazzle assembly, comprising an optical filter element whose optical transmission is electrically controllable, and an electronic control unit including a light sensitive sensor operatively connected to the optical filter element, whereby the electronic control unit is adapted to vary the optical transmission of the optical filter element in response to the amount of light falling on the light sensitive sensor.

PRIOR ART

Anti-dazzle assemblies of this kind are known in the art in various embodiments and variations and are disclosed, for example, in European Patent Publication No. 0,091,514 B1 and in German Patent Publication No. 41 28 291 C2. Up to now, such anti-dazzle assemblies have been used in protective goggles, protective helmets and protective shields or baffles in the field of welding technology. In view of the progressive miniaturization of electronic circuitry, the possibility exists that such anti-dazzle assemblies can be used in sun glasses or in protective helmets for motorcyclists.

As an optical filter element with electrically variable transmission, preferably a liquid crystal cell is used. Usually, this liquid crystal cell forms part of a filter assembly which includes still further filter elements, e.g. such filter elements which limit the pass band of the filter assembly essentially to the visible light. In order to measure the intensity of the light falling onto the filter element, usually there is provided a light sensitive sensor in the form of a photoelectric transducer which can be located either in the optical path of the filter assembly or immediately beside the filter assembly. Moreover, embodiments are known which make use of more than one of these transducers.

For the impression of brightness present in the human eye, essentially the illuminance is authoritative. By means of the light sensitive sensor, the value of the illuminance to be expected at the human eye should be measured, in order to control, based on the measured value of the illuminance, the degree of optical transmission of the electrically controllable filter element with the help of the electronic control unit. Thereby, the electronic control unit can be designed such that its operation or effect starts only when the illuminance exceeds a certain threshold value. This threshold value can be adjusted such that the optical transmission of the filter elements is decreased only in the case when a further increase in illuminance would lead to a dazzling of the eyes. This is to avoid that the field of vision is unnecessarily darkened in the case of a continuously strong, but not dazzling illumination.

The light received from different directions by an optoelectric transducer, e.g. a photo diode or equivalent, usually falls onto the exposed sensor surface with differing light intensity. Particularly in the case of point-shaped light sources with a very pronounced light intensity and high luminance, e.g. in the case of a welding arc, the light intensities in the room area covered by the sensor can locally vary to a great extent. The optoelectric transducer, however, cannot recognize these local differences in light intensities; it rather produces an output signal which corresponds to a average value of the illuminance.

Such a behavior is particularly disadvantageous in the case when the light intensities locally vary to a great extent in the room area covered by the sensor. If a point-shaped light source with an extremely high light intensity in a comparatively dark surrounding area is present, output signals can be produced, due to the afore mentioned averaging, the value thereof being not much higher than the one of an output signal which results from a relatively strong but even illumination of the area covered by the sensor. However, it must be considered that a single very strong point-shaped light source has a much higher dazzling effect than another light source which emits light over a large surface. Under these circumstances, with a conventional sensor, it is extremely difficult to distinguish between the two above mentioned kinds of light sources and to consider their dazzling effect. In the case of a control unit which operates in response to a certain threshold value of the illuminance, the result even can be that, on the one hand, a darkening of the filter element takes not place if a point-shaped light source with high intensity is present and, on the other hand, that the filter element unwantedly darkens in the case of a strong but even room illumination or under the influence of other not relevant disturbing light sources.

OBJECTS OF THE INVENTION

It is an object of the present invention to provide a method for controlling an anti-dazzle assembly of the kind mentioned above which avoids the disadvantages discussed just herein before and which presents a clear and unambiguous criterion for the recognition of the illuminance which creates a dazzling of the human eye.

It is a further object of the present invention to provide a method for controlling an anti-dazzle assembly of the kind mentioned above by means of which a clear and unambiguous distinction can be made between dangerous point-shaped light sources with high intensity to cause the electrically controllable filter element to decrease its optical transmission, and harmless light sources shining even with high intensity, but over a large surface to cause the electrically controllable filter element to keep its condition of high optical transmission.

It is a still further object of the invention to provide an anti-dazzling assembly by means of which the method of the invention can be successfully performed.

SUMMARY OF THE INVENTION

In order to meet these and other objects, the invention provides, according to a first aspect, a method for controlling an anti-dazzle assembly comprising an optical filter element whose optical transmission is electrically controllable, and an electronic control unit including a light sensitive sensor operatively connected to the optical filter element. The electronic control unit is adapted to vary the optical transmission of the filter element in response to the amount of light falling on the light sensitive sensor. Thereby, the light sources in the area covered by the light sensitive sensor is projected on the exposed surface of the light sensitive sensor means. The intensity of the projected light sources is selectively measured by means of a plurality of surface area elements of the exposed surface of the light sensitive sensor. The highest measuring signal is selected and exclusively used for the control of the transmission of the optical filter element.

In this way, it is not only possible to clearly and unambiguously recognize a point-shaped light source which causes a dangerous dazzling; moreover, the control of the electrically controllable filter element as far as its optical transmission is concerned can be greatly simplified.

According to a second aspect, the invention provides an anti-dazzle assembly, comprising an optical filter element whose optical transmission is electrically controllable, and an electronic control unit including a light sensitive sensor operatively connected to the optical filter element. The electronic control unit is adapted to vary the optical transmission of the optical filter element in response to the amount of light falling on the light sensitive sensor.

The anti-dazzle assembly comprises means for projecting the sources of light present in the room area covered by the light sensitive sensor on the exposed surface of the light sensitive sensor. The light sensitive sensor comprises a plurality of optoelectric transducer elements in a grid or screen like arrangement. The output signal of each of the optoelectric transducer elements is individually accessible. The electronic control unit comprises an electronic circuit for detecting and selecting the highest of the output signals delivered by the plurality of optoelectric transducer elements to be used for controlling the optical transmission of the optical filter element.

Preferably, the optoelectric transducer elements are photo diodes which are located on a common semiconductor wafer.

A particularly small embodiment of the anti-dazzle assembly can be realized if at least a portion of the electronic control unit forms, together with the afore mentioned sensor, a single constructive unit.

In a preferred embodiment, the electronic circuit for detecting and selecting the highest of the output signals comprises a plurality of circuit portions each assigned to one of the electric transducer elements. The circuit portions can be located, together with the optoelectric transducer elements, on the common semiconductor wafer.

The aforementioned means for projecting the sources of light present in the room area covered by the light sensitive sensor on the exposed surface of the light sensitive sensor can be a lens located in front of the light sensitive sensor. Under certain circumstances, it may be advisable to provide the light sensitive sensor with a filter for optical radiation, e.g. an UV- or IR-filter, said filter being located in front of the light sensitive sensor.

BRIEF DESCRIPTION OF THE DRAWINGS

In the following, an embodiment of the anti-dazzle assembly of the invention will be further described, with reference to the accompanying drawings, in which.

DETAILED DESCRIPTION OF THE DRAWINGS

Figure 1:
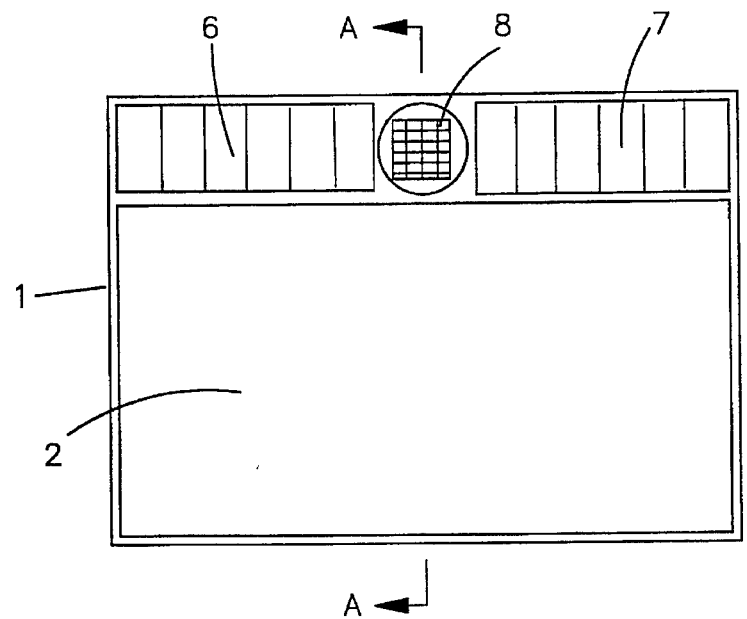
FIG. 1 shows a front view of a anti-dazzle assembly according to the invention in a schematic representation.
Figure 2:
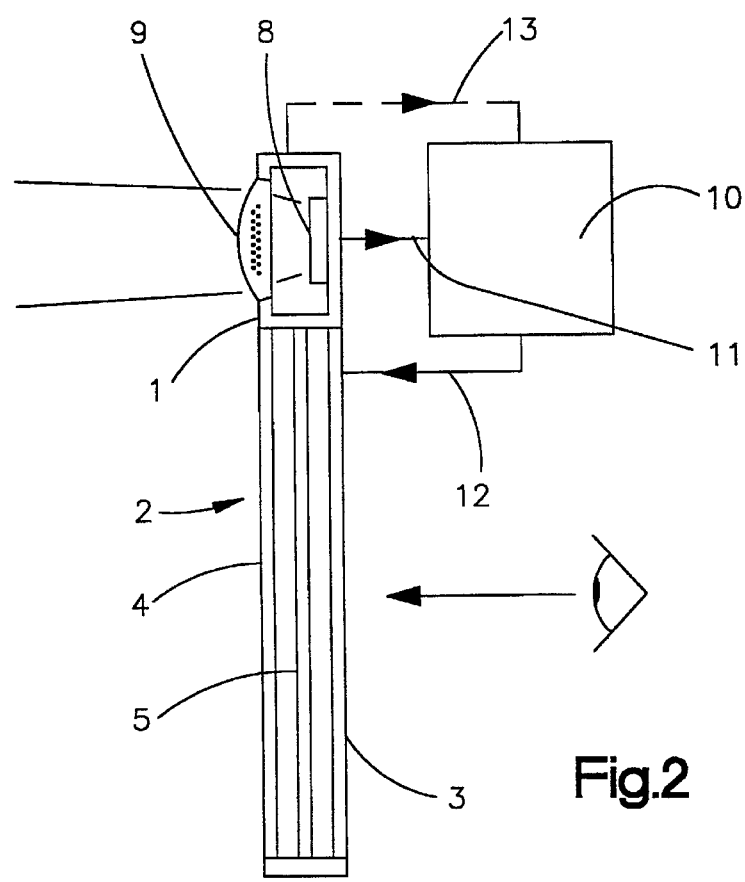
FIG. 2 shows a sectional view of the anti-dazzle assembly of FIG. 1, taken along the line A—A in FIG. 1.

The anti-dazzle assembly shown in FIGS. 1 and 2 comprises a housing frame member 1 provided with an open area serving as a viewing window 2. Inserted into the open area or viewing window 2 of the frame member 1 is a filter element 3 whose optical transmission is electrically controllable, e.g. in the form of a liquid crystal cell well known in the art. In front of the filter element 3, there is provided an ultraviolet filter member 4 and an infrared filter member 5, as is also well known in the art. Above the open area or viewing window 2, solar cells 6 and 7 are provided which serve as a power supply for the entire anti-dazzle assembly. Between the solar cells 6 and 7, a light sensitive sensor 8 is mounted with a lens 9 provided in front thereof, as can be seen in FIG. 2.

Further referring to FIG. 2, there is provided an electronic control unit 10 schematically shown as a black box since such electronic control units are well known in the art. The sensor 8 and the filter 3 with variable optical transmission are operationally connected to the control unit 10. Particularly, the sensor 8 is connected to the electronic control unit 10 via a signal conductor 11 by which the signals from the sensor 8 are transmitted to the control unit 10, and the control unit 10 is connected to the filter 3 by a signal conductor 12 through which the control unit 10 influences the optical transmission of the filter 3 in response to the signal received from the sensor 8. Finally, there is provided a schematically shown conductor 13 for supplying power from the solar cells 6 and 7 to the control unit 10.

Figure 3:
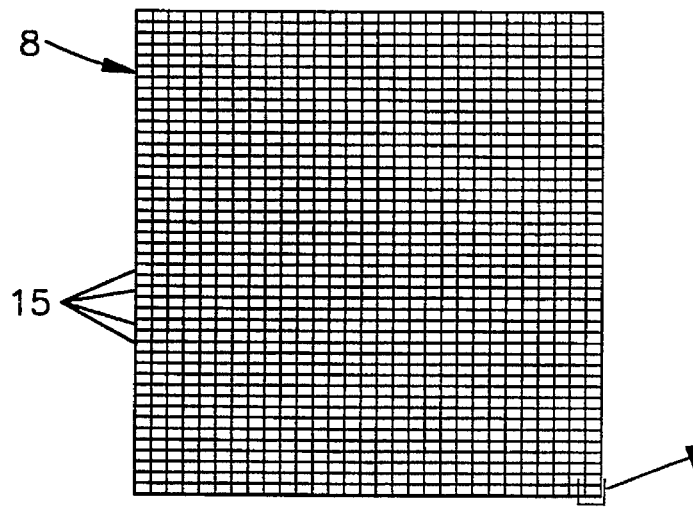
FIG. 3 shows a view of the light sensitive sensor in a greater scale.
Figure 4:
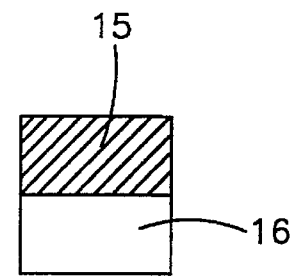
FIG. 4 shows a single sensor element in a still greater scale.

According to FIGS. 3 and 4, the light sensitive sensor 8 comprises a plurality of optoelectric transducer elements 15 in a grid or screen like arrangement, whereby the output signal of each optoelectric transducer element 15 is individually accessible. For example, the sensor may comprise 25 optoelectric transducer elements 15 in a row and 25 optoelectric transducer elements 15 in a column, thus comprising a total of 625 optoelectric transducer elements 15. These optoelectric transducer elements 15, preferably photo diodes, are located on a common semiconductor wafer. Beside each optoelectric transducer element 15, there is provided a space 16 on the wafer adapted to receive not shown electronic components assigned to the adjacent optoelectric transducer element 15 and being part of the common control unit 10.

The afore mentioned electronic components provided in the spaces 16, first and foremost, form or are part of an electronic circuit for the selection of the highest of all the output signals which are produced by the optoelectric transducer elements 15. Such circuit designs per se and the operation thereof are known in the art and disclosed, e.g., in U.S. Pat. No. 5,059,814. Generally spoken, these selection circuits operate such that there is provided a common collection bus to which the output signals of all optoelectric transducer elements are fed. Thereby, the electric potential of the collection bus is determined only by the output signal of the optoelectric transducer element with the highest value, while the effect of the output signals of all other optoelectric transducer elements having lower values are practically completely suppressed.

It is understood that the possibility exists to arrange further electronic components of the electronic control unit 10 on the afore mentioned semiconductor wafer which forms the sensor 8. With the exception of control elements which have to be operated manually, the entire electronic control unit 10 together with the sensor 8 could be designed as a single constructive unit.

Figure 5:
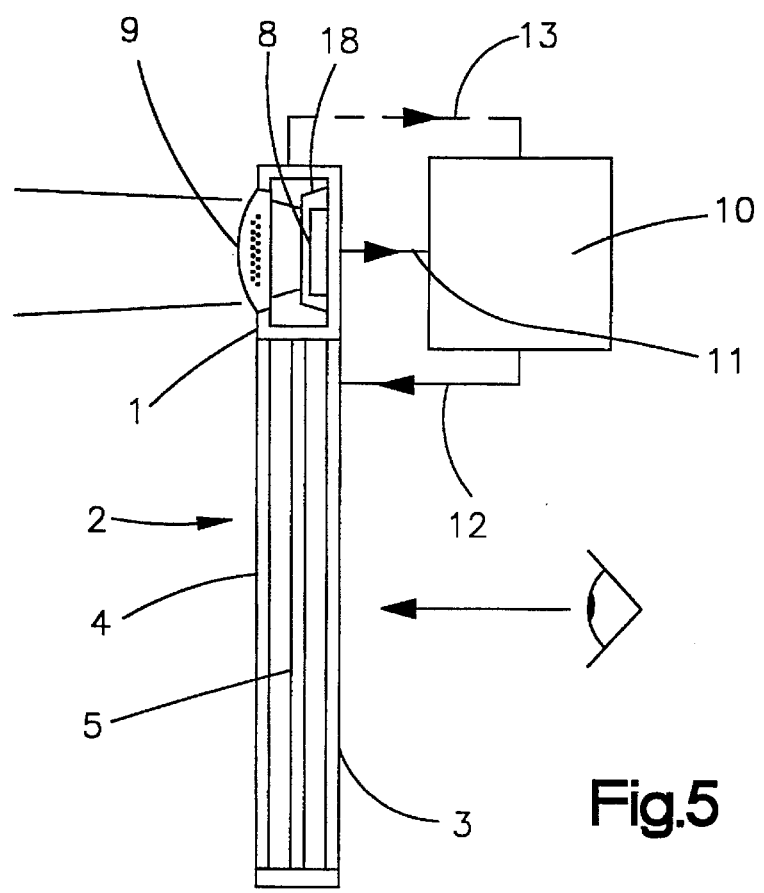
FIG. 5 shows an enlarged sectional view illustrating an embodiment of the present invention.

As shown in FIG. 5, the light sensitive sensor 8 has a filter 18 for optical radiation, e.g. an UV- or IR-filter, located in front of the light sensitive sensor.

What is claimed is:

1. A method for controlling an anti-dazzle assembly comprising an optical filter element whose optical transmission is electrically controllable, and an electronic control means including a light sensitive sensor means operatively connected to said optical filter element, said electronic control means being adapted to vary the optical transmission of said filter element in response to the amount of light falling on said light sensitive sensor means, the method comprising the steps of:

projecting the light sources in the area covered by said light sensitive sensor means on the exposed surface of said light sensitive sensor means;

selectively measuring the intensity of said projected light sources and producing output signals indicative of the intensity of said projected light sources by means of a plurality of surface area elements of said exposed surface of said light sensitive sensor means;

selecting the output signal of a surface area element, said selected surface area element producing an output signal indicating that the portion of said projected light sources exposed to said selected surface area element is more intense than the portions of said projected light sources exposed to the other of said plurality of surface area elements; and using exclusively said output signal of said selected surface area element for the control of the optical transmission of said optical filter element.

2. An anti-dazzle assembly comprising:

an optical filter element whose optical transmission is electrically controllable;

an electronic control means including a light sensitive sensor means operatively connected to said optical filter element, said electronic control means being adapted to vary the optical transmission of said optical filter element in response to the amount of light falling on said light sensitive sensor means;

means for projecting on to the exposed surface of said light sensitive sensor means sources of light present in the room area covered by said light sensitive sensor means;

said light sensitive sensor means comprising a plurality of optoelectric transducer elements in a grid or screen like arrangement, each of said plurality of transducer elements being capable of producing an output signal indicative of the measure of the intensity of the projected light sources exposed to each of said plurality of transducer elements, the output signal of each of said optoelectric transducer elements being individually accessible; and said electronic control means comprising an electronic circuit means for detecting and selecting an output signal, said selected output signal being produced by said transducer element measuring the highest intensity of the projected light sources exposed to said plurality of transducer elements, said electrical control means using said selected output signal being for controlling said optical transmission of said optical filter element.

3. An anti-dazzle assembly according to claim 2 in which said optoelectric transducer elements are photo diodes.

4. An anti-dazzle assembly according to claim 2 further comprising a semiconductor wafer, said optoelectric transducer elements being located on said semiconductor wafer.

5. An anti-dazzle assembly according to claim 2 in which at least a portion of said electronic control means forms, together with said sensor means, a single constructive unit.

6. An anti-dazzle assembly according to claim 4 in which said electronic circuit means for detecting and selecting said selected output signal comprises a plurality of circuit portions each assigned to one of said electric transducer elements, said circuit portions being located, together with said optoelectric transducer elements, on said semiconductor wafer.

7. An anti-dazzle assembly according to claim 2 in which said means for projecting the sources of light present in the room area covered by said light sensitive sensor means on the exposed surface of said light sensitive sensor means is a lens means located in front of said light sensitive sensor means.

8. An anti-dazzle assembly according to claim 2 in which said light sensitive sensor means is provided with a filter for filtering optical radiation, said filter being located in front of said light sensitive sensor means.

9. An anti-dazzle assembly according to claim 2, further comprising solar cell means serving as a power supply for said optical filter element and said control means.

\* \* \* \* \*